(12) United States Patent
Hur et al.

(10) Patent No.: US 9,079,829 B2
(45) Date of Patent: Jul. 14, 2015

(54) METHOD OF PREPARING POWDER OF A SOLID CARBAZIC ACID DERIVATIVE

(71) Applicant: Sogang University Research Foundation, Seoul (KR)

(72) Inventors: Nam Hwi Hur, Seoul (KR); Byeong No Lee, Yongin-si (KR)

(73) Assignee: Sogang University Research Foundation, Seoul (JP)

( * ) Notice: Subject to any disclaimer, the term of this patent is extended or adjusted under 35 U.S.C. 154(b) by 0 days.

(21) Appl. No.: 13/929,201

(22) Filed: Jun. 27, 2013

(65) Prior Publication Data

US 2014/0018573 A1    Jan. 16, 2014

Related U.S. Application Data

(63) Continuation of application No. PCT/KR2011/007573, filed on Oct. 12, 2011.

(30) Foreign Application Priority Data

Dec. 27, 2010  (KR) ........................ 10-2010-0135935

(51) Int. Cl.
*C07C 51/15*     (2006.01)
*C07C 281/02*    (2006.01)

(52) U.S. Cl.
CPC .................................... *C07C 281/02* (2013.01)

(58) Field of Classification Search
CPC .................................................... C07C 281/02
USPC .......................................................... 562/550
See application file for complete search history.

(56) References Cited

U.S. PATENT DOCUMENTS

| | | | |
|---|---|---|---|
| 2,865,714 A | 12/1958 | Robell et al. | |
| 2,878,103 A | 3/1959 | Robell et al. | |
| 3,347,023 A * | 10/1967 | Scott | ............................... 96/158 |
| 3,551,226 A | 12/1970 | Allan et al. | |

FOREIGN PATENT DOCUMENTS

JP           08-134038       *   5/1996

OTHER PUBLICATIONS

JP08-134038, 1996, machine translation.*
International Search Report issued in International App. No. PCT/KR2011/007573, mailed May 8, 2012.

* cited by examiner

*Primary Examiner* — Yevegeny Valenrod
*Assistant Examiner* — Blaine G Doletski
(74) *Attorney, Agent, or Firm* — Greer Burns & Crain Ltd.

(57) ABSTRACT

The present disclosure relates to a method of preparing powder of a solid carbazic acid derivative, which involves inducing a reaction of a liquid hydrazine derivative with carbon dioxide at a high pressure of from about 0.5 MPa to about 100 MPa. During the reaction, the pressure may range from about 0.5 MPa to about 100 MPa. In this regard, although the reaction of the carbon dioxide with the liquid hydrazine derivative occurs when the pressure is adjusted to below than about 0.5 MPa, sticky precipitates in a form of gel are gradually produced but the powder is not produced.

9 Claims, 2 Drawing Sheets

METHOD OF PREPARING POWDER OF A SOLID CARBAZIC ACID DERIVATIVE

This application is a continuation of International Application No. PCT/KR2011/007573 filed on Oct. 12, 2011, claiming the priority based on Korean Patent Application No. 10-2010-0135935 filed on Dec. 27, 2010, the contents of all of which are incorporated herein by reference in their entirety.

TECHNICAL FIELD

The present disclosure relates to a method of preparing powder of a solid carbazic acid derivative.

BACKGROUND ART

Hydrazine ($N_2H_4$) has similar chemical characteristics to those of ammonia ($NH_3$) gas, but is a transparent liquid at a room temperature having the similar melting point, boiling point and density as those of water. Hydrazine has been variously applied to a forming agent for making pores in a polymer, a derivative needed to make agricultural pesticides or medicaments, an oxygen remover from boiler water, a fuel cell, a fuel of a rocket, and so on. Since hydrazine is very poisonous and has high reactivity, it is stored and used in the state of an aqueous solution diluted with water rather than anhydrous hydrazine. Nevertheless, since liquid hydrazine may cause occurrence of fire due to leakage or evaporation or contamination due to rapid reaction with peripheral metals or materials, there has been lots of restriction to its application.

As one solution to the problems of liquid hydrazine, it has been suggested to make and use solid hydrazinium salts in lieu of the hydrazine. The hydrazinium salts can be easily made by adding acids such as sulfuric acid or hydrochloric acid to the liquid hydrazine. For example, when sulfuric acid solution is added to the liquid hydrazine, precipitates are immediately produced and converted into hydrazinium sulfate. These solid hydrazine derivatives are advantageous in that they are in the stable solid phase at a room temperature and can have similar characteristics to those of the liquid hydrazine when they react with other compounds in a solution. However, since the hydrazine salts require a solvent upon reaction, an additional process for separating the solvent after the reaction is necessary. Further, undesired impurities are formed due to residual anions. In addition, since the hydrazine salts exist as a hydrazinium cation in a solution, their reactivity or decomposition ability to generate hydrogen is very poor, compared to hydrazine. Due to the foregoing flaws, application research of the hydrazine salts has been limited, despite that various types of solid hydrazine salts which are highly stable at a room temperature and a normal pressure have been developed.

In order to solve the above-described problems, as disclosed in U.S. Pat. Nos. 3,551,226 and 2,878,103, solid hydrazine was prepared by using carbon dioxide which is flame retardant gas. This method was carried out by blowing carbon dioxide into a cold hydrazine solution at a normal pressure. Once the gas is blown for 15 hours or more, sticky precipitates in which the carbon dioxide and the hydrazine are mixed with each other are gradually produced. However, this resulting product is a solid containing water and mainly consists of carbazic acid ($HCO_2N_2H_3$) and hydrazinium carbazate ($N_2H_5CO_2N_2H_3$). Accordingly, the proportions of the hydrazine and the carbon dioxide are not constant. Further, since the resulting product is very sticky solid, there has been difficulty in obtaining pure solid hydrazine in a powder form through a general drying method.

DISCLOSURE OF THE INVENTION

Problems to be Solved by the Invention

In order to solve the problems of the hydrazine, which is in a liquid state at a room temperature and a normal pressure, and the solid hyrazinium salt materials, the inventors of the present disclosure developed powder of a solid carbazic acid derivative, which has the same excellent reactivity as that of the anhydrous hydrazine, exists in a stable solid state at a room temperature and a normal pressure, and can be easily used without requiring a solvent. That is, the purpose of the present disclosure is to provide powder of a solid carbazic acid derivative.

Means for Solving the Problems

The present disclosure has been invented to solve the problems of the hydrazine which is in a liquid state at a room temperature and a normal pressure, and the solid hyrazinium salts which have been developed to the present. To this end, the present disclosure prepares powder of a carbazic acid derivative by introducing high pressure carbon dioxide to induce a reaction between a liquid hydrazine derivative with carbon dioxide. By using carbon dioxide at a high pressure, the present disclosure can provide a technique of preparing powder of pure carbazic acid derivative in which no water and by-product exist. The high pressure means from about 0.5 MPa to about 100 MPa.

Effect of the Invention

In the method of preparing powder of a solid carbazic acid derivative according to the present disclosure, since carbon dioxide is used at the high pressure of from about 0.5 MPa to about 100 MPa, carbon dioxide and a hydrazine derivative are rapidly reacted with each other and easily converted into a solid carbazic acid derivative. Accordingly, the time and energy necessary for solidification can be significantly reduced. Furthermore, since residual water contained in the liquid hydrazine derivative can be minimized, it is possible to prepare pure powder of a solid carbazic acid derivative, in which water and by-product rarely exist. The method of preparing powder of a solid carbazic acid derivative has not been conventionally known and corresponds to a breakthrough technology.

The powder of a solid carbazic acid derivative, which has been developed by the present disclosure, provides the following advantages: (i) since the solid powder is in the stable solid state at a room temperature, it is convenient in storage and utilization, and is not hazardous; (ii) since the solid powder is easily decomposed into hydrazine and carbon dioxide upon a reaction, it has the same excellent reactivity as that of anhydrous hydrazine; (iii) the solid powder can be used even in the environment that no solvent exists; (iv) since the solid powder does not contain water, it can be used in an anhydrous environment; and (v) the solid powder can be used as a solid fuel that can generate hydrogen.

BEST MODE FOR CARRYING OUT THE INVENTION

Figure 1:
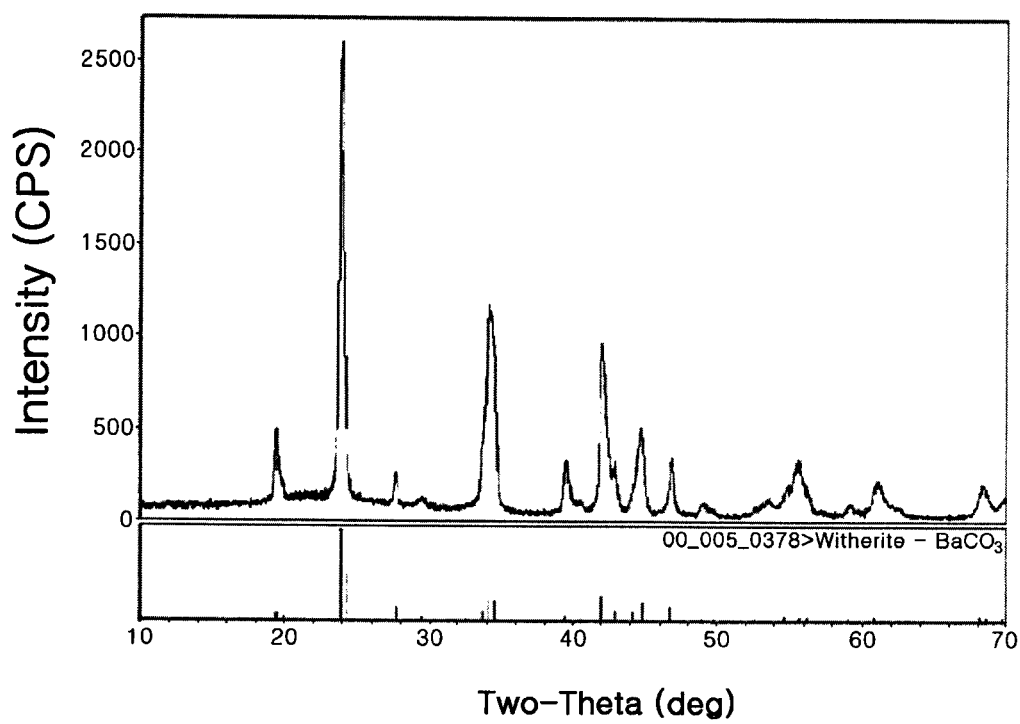
FIG. 1 is a result of X-ray diffraction (XRD) analysis of a decomposition product of powder of a solid carbazic acid in accordance with an Example of the present disclosure.

The present disclosure relates to a method of preparing powder of a solid carbazic acid derivative by reacting a liquid hydrazine derivative and carbon dioxide under a condition of a high pressure of from about 0.5 MPa to about 100 MPa.

In the above-described reaction, the pressure is preferably from about 0.5 MPa to about 100 MPa. When the pressure is adjusted to below than about 0.5 MPa, the reaction of the carbon dioxide with the liquid hydrazine derivative occurs, but sticky precipitates in a gel form are gradually produced while a powder form is not produced. The precipitates remain in the sticky state even when the precipitates are washed with alcohol several times and dried in vacuum. The solid products containing water are a mixture consisting of carbazic acid and hydrazinium carbazate. More preferably, the condition of the high pressure may be from about 1 MPa to about 50 MPa.

The hydrazine derivative can be represented by the following Chemical Formula 1:

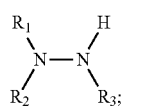

[Chemical Formula 1]

wherein in Chemical Formula 1, each of $R_1$ to $R_3$ is independently hydrogen, an alkyl group, a cycloalkyl group, a phenyl group, nitro-phenyl group or an aryl group.

The reaction in the condition of the high pressure may be conducted under a solvent-free condition, or under water, alcohol of $C_1$ to $C_{12}$, ether of $C_2$ to $C_{12}$ or a mixture solvent thereof. In particular, when the reaction is conducted under an alcohol solvent of $C_1$ to $C_{12}$, a more highly pure carbazic acid derivate can be obtained.

The temperature in the reaction under the condition of the high pressure may be adjusted to from about −10° C. to about 500° C. This is because the reaction may not be fully conducted at the temperature below than about −10° C., and the reaction rate is not improved even when the temperature exceeds about 500° C. More preferably, the temperature may be from about 0° C. to about 300° C.

The hydrazine derivative represented by Formula 1 may be an anhydrous hydrazine derivative or a hydrate thereof.

As the hydrazine derivative represented by Chemical Formula 1, any one that can produce a carbazic acid derivative through a reaction with carbon dioxide may be used without limitation. In this regard, hydrazine ($N_2H_4$), mono-methyl hydrazine ($CH_3N_2H_3$), dimethyl hydrazine (($CH_3$)$_2N_2H_2$), phenylhydrazine ($C_6H_5N_2H_3$) or 2,4-di-nitro-phenyl hydrazine ($C_6H_3(NO_2)_2N_2H_3$) may be used.

A water content in a hydrate of the hydrazine derivative may be from about 1 wt % to about 99 wt %. More preferably, the water content may be from about 30 wt % to about 90 wt %.

As carbon dioxide, gas-phase carbon dioxide or liquid-phase carbon dioxide may be used. Furthermore, carbon dioxide in a supercritical state or solid-phase dry ice may be used.

A step for reducing the pressure to the level of from about 0.01 MPa to about 0.1 MPa after the reaction in the condition of the high pressure to evaporate excess carbon dioxide may be added.

Even when the powder of a solid carbazic acid derivative is prepared through the above-described method, components such as water may remain in the residual powders. It is possible to remove such components by washing the residual powders with a solvent which can be mixed with water. For example, it is possible to remove the components by washing them with a solvent such as alcohols, tetrahydrofurane (THF), ethers, and dimethylformamide (DMF) or a mixture thereof. That is, as a purification process of the powder of a solid carbazic acid derivative, a process for washing the residual components with alcohols of $C_1$ to $C_{12}$, tetrahydrofurane (THF), ethers, dimethylformamide (DMF) or a mixture solution thereof may be added.

As described above, it is possible to preparing the powder of a solid carbazic acid derivative by reacting the liquid hydrazine derivative with carbon dioxide at a high pressure. The powder has the structure of the carbazic acid form obtained from the reaction of the hydrazine and the carbon dioxide at 1:1. Particularly, in case of using a hydrazine hydrate represented by the chemical formula of $N_2H_4 \cdot H_2O$ as the hydrazine derivative, the resulting product is a compound having the carbazic acid structure and can be represented by the chemical formula of $HCO_2N_2H_3$.

Hereinafter, the present disclosure will be described in more detail with reference to examples. However, the examples are described only for the purpose of illustration, and it should be understood that the present disclosure is not limited to the examples.

Example 1

Preparation of Powder of a Solid Carbazic Acid Using Supercritical Carbon Dioxide A solid carbazic acid powder ($HCO_2N_2H_3$) was prepared by putting 3 mL of a hydrazine hydrate solution having a water content of approximately 36 wt % into a reactor and adjusting a pressure of carbon dioxide and a temperature of the reactor. A reaction was conducted in the supercritical state that the pressure of carbon dioxide is 7.4 MPa or more, and the temperature of the reactor is 32° C. or more. The temperature was adjusted by placing a high pressure reactor in an oil bath. The reaction was conducted for 5 hours. After the reaction, the pressure was reduced to remove residual carbon dioxide. Remaining solid was washed 5 times with 20 mL methanol and dried in vacuum for 3 hours to obtain the solid carbazic acid powder.

When the obtained solid carbazic acid powder was put into water, it was melted while generating gas. The generated gas was easily reacted with barium hydroxide ($Ba(OH)_2$) thereby to form barium carbonate ($BaCO_3$). The components of the remaining solution were analyzed by a mass spectrometer to confirm that only hydrazine existed in the solution. This powder corresponds to a compound represented by the chemical formula of carbazic acid ($HCO_2N_2H_3$) from the results of the elemental analysis and the mass spectrometric analysis. A yield of the obtained $HCO_2N_2H_3$ was at least 98% based on the used hydrazine hydrate.

Result of elemental analysis (unit %) for the resulting product $HCO_2N_2H_3$

Elements (calculated value, experimental value): C(15.79, 15.75), H(5.30, 5.31), N(36.84, 36.90)

Mass spectrometric analysis, MS (EI+)m/z=32[M]+, 31, 29, 17, 15

Example 2

Preparation of a Solid Carbazic Acid Powder Using Dry Ice

Using the same method as in Example 1, the reaction was completed by using dry ice which is solid carbon dioxide as a carbon dioxide supply source. The reaction was conducted by putting 3 mL of a hydrazine hydrate solution having a water content of approximately 36 wt % into a reactor, adding 15 g of dry ice thereto, and placing the reactor in an oil bath which had been adjusted to reach approximately 100° C. At this time, the pressure was from 10 MPa to 12 MPa. Under this condition, the reaction was conducted for approximately 12 hours. After the reaction, the pressure was reduced to remove residual carbon dioxide. A small amount of the remaining water was washed with methanol and dried in vacuum to obtain powder. To confirm properties of the obtained carbazic acid powder, elemental analysis and mass spectrometric analysis were carried out the same as in Example 1.

It was confirmed that this solid powder is represented by the chemical formula of carbazic acid ($HCO_2N_2H_3$) from the results of the elemental analysis and the mass spectrometric analysis, which is the same compound as obtained in Example 1. A yield of the obtained $HCO_2N_2H_3$ was at least 98% based on the used hydrazine hydrate.

Result of elemental analysis (unit %) for the resulting product $HCO_2N_2H_3$

Elements (calculated value, experimental value): C(15.79, 15.73), H(5.30, 5.32), N(36.84, 36.92)

Mass spectrometric analysis, MS (EI+)m/z=32[M]+, 31, 29, 17, 15

Example 3

Preparation of a Solid Carbazic Acid Powder Using Carbon Dioxide Gas

Using the same method as in Example 1, carbon dioxide gas was added. The solid carbazic acid powder was obtained at a pressure of 10 MPa and a temperature of 100° C. To confirm properties of the obtained carbazic acid powder, elemental analysis and mass spectrometric analysis were carried out the same as in Example 1.

It was confirmed that this solid powder is represented by chemical formula of carbazic acid ($HCO_2N_2H_3$) from the results of the elemental analysis and the mass spectrometric analysis, which is the same compound as obtained in Example 1. A yield of the obtained $HCO_2N_2H_3$ was at least 96% based on the used hydrazine hydrate.

Result of elemental analysis (unit %) for the resulting product $HCO_2N_2H_3$

Elements (calculated value, experimental value): C(15.79, 15.69), H(5.30, 5.36), N(36.84, 37.02)

Mass spectrometric analysis, MS (EI+)m/z=32[M]+, 31, 29, 17, 15

Example 4

Preparation of a Solid Carbazic Acid Powder Using Water as a Solvent

A solid carbazic acid powder was prepared by putting a mixture of 0.5 mL hydrazine hydrate having a water content of approximately 36 wt % and 2 mL distilled water into a reactor, and adjusting a pressure of carbon dioxide and a temperature of the reactor. Powder of a solid carbazic acid derivative was obtained at a pressure of 10 MPa and a temperature of 100° C. To confirm properties of the obtained carbazic acid powder, elemental analysis and mass spectrometric analysis were carried out the same as in Example 1.

It was confirmed that this solid powder is represented by the chemical formula of carbazic acid ($HCO_2N_2H_3$) from the results of the elemental analysis and the mass spectrometric analysis, which is the same as obtained in Example 1. A yield of the obtained $HCO_2N_2H_3$ was at least 98% based on the used hydrazine hydrate Result of elemental analysis (unit %) for the resulting product $HCO_2N_2H_3$ Elements (calculated value, experimental value): C(15.79, 15.71), H(5.30, 5.34), N(36.84, 36.59)

Mass spectrometric analysis, MS (EI+)m/z=32[M]+, 31, 29, 17, 15

Example 5

Preparation of a Solid Carbazic Acid Powder Using Methanol as a Solvent

Using the same method as in Example 1, powder of a solid carbazic acid derivative was obtained by putting 3 mL hydrazine hydrate and 10 mL methanol together into the reactor. To confirm properties of the obtained carbazic acid powder, elemental analysis and mass spectrometric analysis were carried out the same as in Example 1.

It was confirmed that this solid powder is represented by the chemical formula of carbazic acid ($HCO_2N_2H_3$) from the results of the elemental analysis and the mass spectrometric analysis, which is the same as obtained in Example 1. A yield of the obtained $HCO_2N_2H_3$ was at least 98% based on the used hydrazine hydrate.

Result of elemental analysis (unit %) for the resulting product $HCO_2N_2H_3$

Elements (calculated value, experimental value): C(15.79, 15.81), H(5.30, 5.33), N(36.84, 36.61)

Mass spectrometric analysis, MS (EI+)m/z=32[M]+, 31, 29, 17, 15

Example 6

Preparation of a Solid Carbazic Acid Powder Using Ethanol as a Solvent

Using the same method as in Example 1, a solid carbazic acid powder was obtained, by using 10 mL ethanol, instead of methanol. To confirm properties of the obtained carbazic acid powder, elemental analysis and mass spectrometric analysis were carried out the same as in Example 1.

It was confirmed that this solid powder is represented by the chemical formula of carbazic acid ($HCO_2N_2H_3$) from the results of the elemental analysis and the mass spectrometric analysis, which is same as obtained in Example 1. A yield of the obtained $HCO_2N_2H_3$ was 98% based on the used hydrazine hydrate.

Result of elemental analysis (unit %) for the resulting product $HCO_2N_2H_3$

Elements (calculated value, experimental value): C(15.79, 15.84), H(5.30, 5.33), N(36.82, 35.91)

Mass spectrometric analysis, MS (EI+)m/z=32[M]+, 31, 29, 17, 15

Example 7

Preparation of a Solid Phenyl Carbazic Acid Powder Using Supercritical Carbon Dioxide Using the same method as in Example 1, a solid carbazic acid powder was prepared, by using phenyl hydrazine ($C_6H_5N_2H_3$) as a hydrazine derivative, instead of the hydrazine hydrate. After the preparation, the pressure was reduced to remove residual carbon dioxide. The remaining solid was washed 5 times with 20 mL methanol and dried in vacuum for 3 hours to obtain a solid phenyl carbazic acid derivative.

From the results of analyzing components in the solution obtained by melting the dried powder of the solid phenyl carbazic acid derivative in $CDCl_3$ through $^1H$ NMR, it was confirmed that only carbon dioxide and the phenyl hydrazine existed in the solution. A yield of the obtained $C_6H_5N_2H_2CO_2H$ was 99% based on the used phenyl hydrazine.

Result of elemental analysis (unit %) for the resulting product $C_6H_5N_2H_2CO_2H$ Elements (calculated value, experimental value): C(55.25, 55.18), H(5.30, 5.23), N(18.42, 18.31)

$^1H$ NMR (400 MHz, $CDCl_3$, 27° C.) δ=7.25 (m, 2H, phenyl), 6.83 (m, 3H, phenyl), 5.21 (br s, 1H, —NH), 3.58 (br s, 2H, $NH_2$)

Comparative Example 1

Preparation of a Carbazic Acid Solid Using Carbon Dioxide at a Normal Pressure Using the same method as in Example 1, the condition of the pressure and the temperature was adjusted, and a round flask was used, instead of the high pressure reactor. 3 mL of a hydrazine hydrate solution having a hydrazine content of approximately 64 wt % was put into the cold round flask immersed in an ice container, and carbon dioxide of a normal pressure (0.1 MPa) was blown into the solution. After 8 hours, a gel was gradually formed in the transparent solution. When carbon dioxide was further blown into the solution for 10 hours or more, white sticky solid was produced. This solid was washed with methanol in the same manner as in Example 1. The solid in the gel form was dried in vacuum. Even after the drying, hydrazine in the slightly sticky state was obtained.

An obtained yield was approximately 85% based on the used hydrazine hydrate. The result of the elemental analysis was inconsistent with the composition of the same resulting product $HCO_2N_2H_3$ as that in Example 1. Further, the ratios of the elements were not constant. Thus, it is assumed that the resulting product is solid containing water as well as other materials such as $NH_2NH_3.CO_2.NH_2NH_3$/in addition to carbazic acid ($HCO_2N_2H_3$).

Result of elemental analysis (unit %) for the resulting product $HCO_2N_2H_3$

Elements (calculated value, experimental value): C(15.79, 13.83), H(5.30, 6.56), N(36.84, 39.72)

Mass spectrometric analysis, MS (EI+)m/z=32[M]+, 31, 29, 17, 15

Experimental Example 1

Study of X-Ray Diffraction (XRD) Pattern for a Decomposition Product of the Solid Carbazic Acid Powder 0.038 g (0.5 mmol) of the solid powder prepared by the same method as in Example 1 was put into 100 mL of a $Ba(OH)_2$ solution and sealed immediately. The $Ba(OH)_2$ aqueous solution was prepared by melting 0.1575 g (0.5 mmol) $Ba(OH)_2$ in 100 mL water. This mixture solution was stirred at 50° C. for 10 hours. Thereafter, the solution was concentrated to mL under a reduced pressure. As-formed white precipitates were filtered by a filter, and water was removed by using a 20 mL methanol solution. This process was repeated 3 times to obtain 0.095 g (0.48 mmol) white precipitates. As a result of the XRD analysis, it was confirmed that the precipitates were $BaCO_3$. A yield of the resulting obtained product was 96% based on the used powder of a solid carbazic acid derivative. This can be confirmed from the XRD data of FIG. 1. Yields of the powders of solid carbazic acid derivatives prepared in Examples 2 to 7 and Comparative Example 1 were also measured in the same manner as described above. The results are shown in Examples 2 to 7 and Comparative Example 1, respectively.

Experimental Example 2

Figure 2:
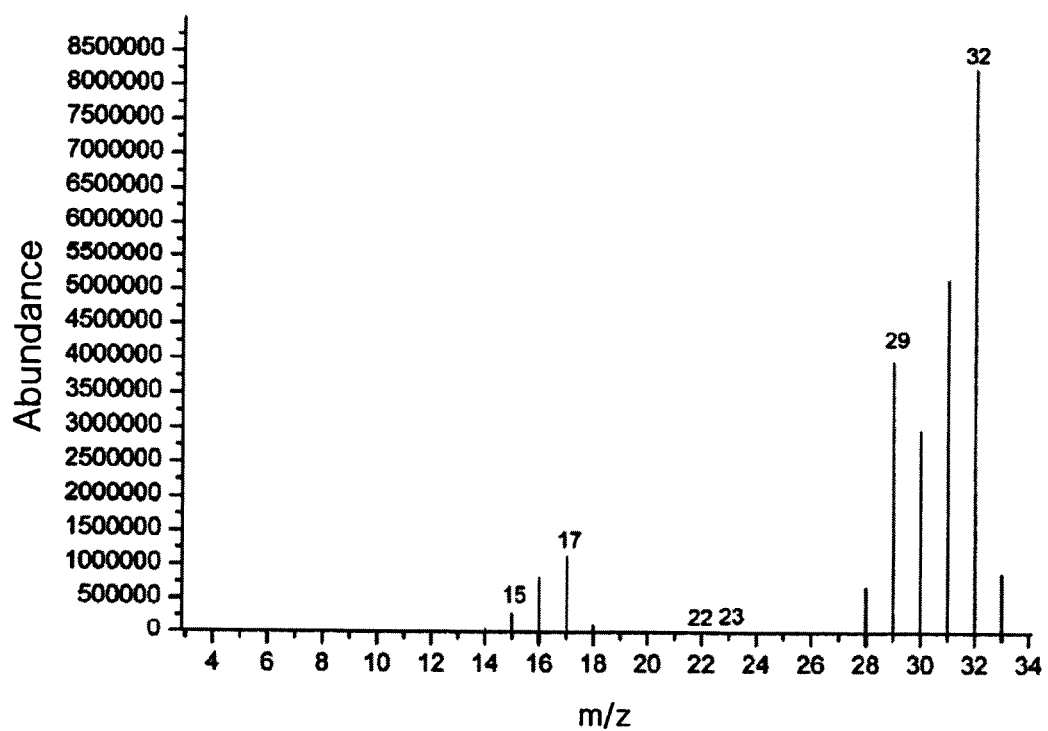
FIG. 2 is a result of gas chromatography/mass spectrometric (GC/MS) analysis of a decomposition product of powder of a solid carbazic acid in accordance with an Example of the present disclosure.

GC/MS Study of a Decomposition Product of the Solid Carbazic Acid Powder 0.5 g of the solid carbazic acid powder prepared by the same method as used in Example 1 was put into a 25 mL round flask, and 5 mL distilled water was added thereto. The white powders were gradually melted while generating foams to become a transparent solution. As a result of the GC/MS analysis, it was confirmed that the solution was completely converted into hydrazine ($H_2NNH_2$). This can be confirmed from the GC/MS data of FIG. 2. The powders of solid carbazic acid derivatives prepared in Examples 2 to 7 and Comparative Example 1 were also measured by the same method as described above. The results are shown in Examples 2 to 7 and Comparative Example 1, respectively.

What is claimed is:

1. A method of preparing powder of a solid carbazic acid derivative, comprising:
   reacting a liquid hydrazine derivative represented by following Formula 1 with carbon dioxide in a supercritical state under a condition of a high pressure of from 7.38 MPa to 100 MPa:

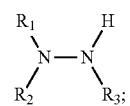

[Formula 1]

wherein in Formula 1, each of $R_1$ to $R_3$ is independently hydrogen, an alkyl group, a cycloalkyl group, a phenyl group, nitro-phenyl group or an aryl group.

2. The method of preparing powder of a solid carbazic acid derivative of claim 1,
   wherein the reaction in the condition of the high pressure is conducted under a solvent-free condition, or under water, alcohol of $C_1$ to $C_{12}$, ether of $C_2$ to $C_{12}$, or a mixture solvent thereof.

3. The method of preparing powder of a solid carbazic acid derivative of claim 1,
   wherein the high pressure is from 7.38 MPa to 50 MPa.

4. The method of preparing powder of a solid carbazic acid derivative of claim 1,
   wherein the temperature in the reaction is from 30.95° C. to 500° C.

5. The method of preparing powder of a solid carbazic acid derivative of claim 1,
   wherein the hydrazine derivative represented by Formula 1 is an anhydrous hydrazine derivative or a hydrate thereof.

6. The method of preparing powder of a solid carbazic acid derivative of claim 1,
   wherein the hydrazine derivative represented by Formula 1 is hydrazine, mono-methyl hydrazine, dimethyl hydrazine, phenylhydrazine, nitro-phenyl hydrazine, or derivatives thereof.

7. The method of preparing powder of a solid carbazic acid derivative of claim 5,
   wherein a water content in the hydrazine derivative hydrate is from 1 wt % to 99 wt %.

8. The method of preparing powder of a solid carbazic acid derivative of claim 1,
   wherein the method further includes a step for reducing the pressure to the value of from 0.01 MPa to 0.1 MPa so as to evaporate excess carbon dioxide after the reaction under the condition of the high pressure.

9. The method of preparing powder of a solid from carbazic acid derivative of claim 1 or 8,
   wherein the method further includes a washing step with alcohols of $C_1$ to $C_{12}$, tetrahydrofurane, ethers, dimethylformamide or a mixture solution thereof, as a purification process of the powder of a solid carbazic acid derivative.

\* \* \* \* \*